US005532951A

United States Patent [19]
Ohlsson et al.

[11] Patent Number: 5,532,951
[45] Date of Patent: Jul. 2, 1996

[54] DEVICE FOR ELIMINATING RINGING IN FILTERED ECG SIGNALS

[75] Inventors: Thomas Ohlsson, Haesselby; Peter Karlsson, Stockholm, both of Sweden

[73] Assignee: Siemens-Elema AB, Solna, Sweden

[21] Appl. No.: 266,233

[22] Filed: Jun. 27, 1994

[30] Foreign Application Priority Data

Jul. 16, 1993 [SE] Sweden ................................. 9302433

[51] Int. Cl.$^6$ .......................... G06F 17/10; A61B 5/0402
[52] U.S. Cl. ................. 364/724.17; 364/413.06
[58] Field of Search .................. 364/724.17, 724.01, 364/413.06; 128/696

[56] References Cited

U.S. PATENT DOCUMENTS

| | | | |
|---|---|---|---|
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Strick | 128/705 |
| 4,939,576 | 7/1990 | Campbell | 364/724.01 |
| 5,025,794 | 6/1991 | Albert et al. | 128/696 |
| 5,139,027 | 8/1992 | Lindecrantz | 128/696 |
| 5,144,569 | 9/1992 | Kunold | 364/724.01 |
| 5,211,179 | 5/1993 | Haberl et al. | 128/702 |
| 5,269,313 | 12/1993 | DePinto | 128/696 |
| 5,341,811 | 8/1994 | Cano | 128/696 |
| 5,402,795 | 4/1995 | Reichl | 128/696 |

FOREIGN PATENT DOCUMENTS 1556512  12/1976  United Kingdom.
WO93/05573  3/1993  WIPO.

OTHER PUBLICATIONS

"Detection of Late Potentials by Adaptive Filtering," Shelton et a., J. of Electrocardiology, vol. 23, (1990): Suppl., pp. 138–143.
"Highpass Filters for Detecting Late Potentials," Link et al, Proc. Computers in Cardiology (1992), pp. 159–162.

*Primary Examiner*—David H. Malzahn
*Attorney, Agent, or Firm*—Hill, Steadman & Simpson

[57] ABSTRACT

A device for eliminating ringing in filtered ECG signals includes an analog-to-digital for converting the ECG input signals into a series of digital values, and a filter unit connected to the output of the analog-to digital converter. The filter unit includes a recursive IIR-filter and a subsequent allpass filter with a phase shift which is equal to twice the phase shift of the IIR filter. The allpass filtering is performed time-reversed with respect to the IIR filtering. In a method for producing an allpass filter, for use in the above device, having a phase shift which is equal to twice the phase shift of an IIR filter, the IIR filter having zero points situated on the unity circle in the Z-plane, the zero points of the IIR filter are replaced by new zero points obtained by reflecting the poles of the filter in the unity circle in the Z-plane.

5 Claims, 1 Drawing Sheet

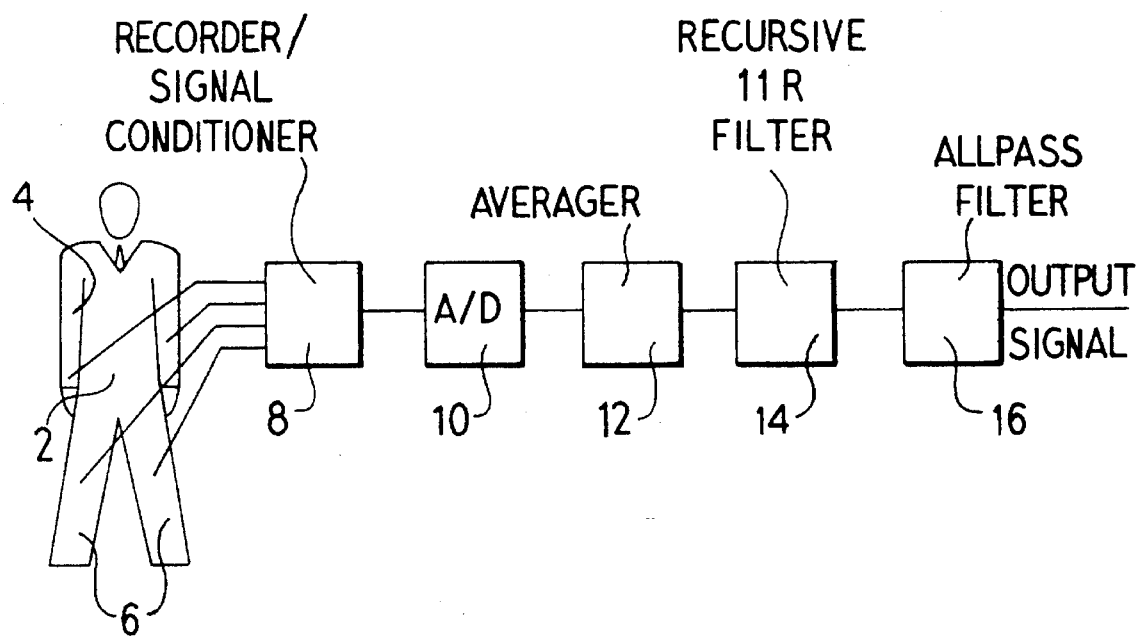

DEVICE FOR ELIMINATING RINGING IN FILTERED ECG SIGNALS

BACKGROUND OF THE INVENTION

1. Field of the Invention

The present invention is directed to a device for eliminating ringing in filtered ECG signals, of the type having an analog-to digital converter for converting analog ECG input signals into a series of digital values, and a filter unit connected to the output of the analog-to digital converter. The present invention is also directed to a method for producing an allpass filter, for use in such a device, having a phase shift which is equal to twice the phase shift of an IIR filter having zero points which are situated on a unity circle in the Z-plane.

2. Description of the Prior Art

Different kinds of signal filtering are required for the analysis of ECG signals.

The ECG signal recorded between two electrodes placed on the body of a patient, for example, on the arms and legs, also contains a d.c. potential, in addition to the ECG signal. The d.c. potential may be much larger than the ECG signal. Low-frequency signals may also be present in the measured signal. The d.c. potential or the low-frequency components vary because of relative movements of the body of the patient and the electrode due, for example, to the patient's breathing movements.

Two-pass filtering is a known technique for removing these d.c. components and low-frequency components from the ECG signal. For this purpose, filtering with a linear phase is accomplished by conducting both forward and backward filtering of the signal employing a filter having a non-linear phase characteristic as described, for example, in United Kingdom Application 1 556 512, which describes such filtering using analog filters. A linear phase characteristic is desirable for the filtering, because phase distortion is then eliminated, which is the cause of minor distortions in the morphology of the ECG signal. A disadvantage of filtering with a linear phase characteristic, however, is that such filtering does not eliminate the problem of ringing arising in the filtered signal. The morphology of the waveforms or signal components produced by ringing depend on the transfer function of the filter, and will persist in the filtered signal. A so-called "FIR" (finite impulse response) filter can alternatively be used for providing a filter having a linear phase characteristic, but the steepness of the slope of the filter must be sacrificed if the filter is to be implemented in a device having limited memory or limited computational capacity.

The presence of high-frequency signals with small amplitudes on the microvolt level at the end of the QRS complex in post-infarction patients has been shown to be a good indication of the presence of an increased risk of future life-threatening ventricular arrhythmias, see European Heart Journal (1991), Vol. 12, pp. 473–480. High-pass filtering is needed in order to identify and analyze these late potentials. The creates the problem that the QRS signal itself induces ringing in the filtered signal, and this ringing masks any late potentials which may be present in the measured signal. Several proposals to solve this problem have been suggested. In an article by Link et al., "High-pass Filters for Detecting Late Potentials", Proc. Computers in Cardiology 1992, pp. 159–162, suggest the use of a non-recursive, monotonic, binomial, high-pass filter for detecting late potentials.

U.S. Pat. No. 4,422,459 proposes a technique for identifying the presence or absence of a time segment containing high-frequency signals in the latter part of a patient's QRS complex, and for measuring the magnitude of this segment. The measured analog ECG signals are converted into digital signals, and normal QRS complex signals are averaged over a hundred or more heartbeats in order to obtain a relatively noise-free complex. The averaged complex is then subjected to high-pass filtering in a fourth order Butterworth filter. The filtering is performed in the forward direction until the start of QRS+40 ms, and is then conducted in the backward direction from the end of the complex to the same point. The two filtered signals are then combined to form a resultant filtered signal, in which ringing is avoided immediately before and after the QRS, complex. The waveform of the QRS complex itself, however, is slightly altered, and therefore the avoidance of ringing is achieved only at the expense of producing an "erroneous" signal in the QRS complex itself. The resultant filtered signal is then subjected to measurements to ascertain the presence or absence of the aforementioned late potentials. The disadvantage of this technique is that the resultant filtered curve is discontinuous, and the measured version of the QRS complex obtained in this manner has an erroneous energy content as compared to the "true" QRS complex.

A system is disclosed in U.S. Pat. No. 4,458,691 for high-pass forward filtering of ECG signals for detecting late potentials. In this system, an adaptive high-pass filter for selective filtering of different segments of the QRS complex is employed to solve the problem of ringing. This technique also has several disadvantages. Ringing is not completely eliminated, and in order to reduce the ringing effect as much as possible, short FIR filters with a linear phase are used, which poorer frequency division.

Another technique for detecting late potentials by means of forward filtering of the ECG signal is disclosed in U.S. Pat. No. 4,458,692. In this method, the filter gain is regulated dependent on the magnitude of the input signal in an effort to solve the problem of ringing. The signal which controls the gain can be the output signal from a filter using the QRS signal as in input signal and, for example, the impact of the R-spike on the output signal, and thus on the ringing arising after the R-spike, can be limited if the gain in the filter is limited when the input signal rises above a defined level. This method also has the disadvantage of failing to eliminate all ringing, and a steep filter slope, which is otherwise desirable, must be sacrificed.

A method is also disclosed in U.S. Pat. No. 4,492,235 for detecting late potentials by means of forward filtration of the QRS signal, wherein adaptive high-pass filtering is also employed to address the problems of ringing.

Another method for forward filtration of late potentials is disclosed in U.S. Pat. No. 5,025,794, wherein sampled values of the QRS complex are subjected to both forward and backward filtering, with the filtered signals being added, and the summed signal is then smoothed to yield signal components corresponding to the late potential. The method disclosed in U.S. Pat. No. 5,025,794, however, is very complicated.

SUMMARY OF THE INVENTION

It is an object of the present invention to provide a device for eliminating ringing in filtered ECG signals, wherein the above-identified disadvantages in the prior art are avoided.

It is a further object of the present invention to provide a method for producing an allpass filter suitable for use in a device for eliminating ringing in filtered ECG signals.

The above objects are achieved in accordance with the principles of the present invention in a device wherein the measured ECG signals are supplied as an input to an analog-to digital converter, which generates a series of digital signals corresponding to the analog signals, these digital signals being supplied to a recursive IIR (infinite impulse response) filter, the output of the IIR filter being supplied to an allpass filter. The allpass filter has a phase shift which is equal to twice the phase shift of the IIR filter, and the allpass filtering takes place time-reversed with respect to the IIR filtering. A method for producing an allpass filter suitable for use in the above device, having a phase shift which is equal to twice the phase shift of the IIR filter, the IIR filter having zero points which are situated on a unity circle in the Z-plane, includes the step of replacing the zero points of the IIR filter by new zero points obtained by reflecting the poles of the IIR filter in the unity circle in the Z-plane.

The device according to the invention thus has an allpass filter with a phase shift which exactly corresponds to twice the phase shift of the original filter which created the ringing which is to be eliminated. The allpass filtering is conducted to the signal to be analyzed in a time-reversed direction with respect to the original filtering direction. In this manner, ringing is eliminated in an advantageous manner. The device according to the invention permits late potentials to be detected in a simple manner after the signal has been filtered in the forward direction using the recursive high-pass filter and without any restriction on the steepness of the filter. The device according to the invention can also be advantageously used for delimiting and classifying the waveform of the QRS complex and for determining the ST level.

It should be noted that the result of filtering in the recursive filter, and the subsequent time-reserved allpass filtering, do not filtering with a linear phase characteristic, but instead constitute filtering with a phase response which is negated in relation to the phase response of the recursive filter. This is an optimum characteristic for complete elimination of ringing in the applications in question. The total phase shift in the device according to the invention is thus the same as the phase shift which occurs in backward filtering of the signal using the recursive IIR filter. Thus, any signal waveforms due to ringing are "shifted" away from the area of interest according to the same principle as in backward filtering, even though the original filtering was performed in the forward direction in the conventional manner.

DESCRIPTION OF THE DRAWINGS

The single FIGURE shows an exemplary embodiment of a device for eliminating ringing in an ECG signal, constructed and operating in accordance with the principles of the present invention.

DESCRIPTION OF THE PREFERRED EMBODIMENTS

An ECG is recorded as the potential between electrodes on the body 2 of a patient, for example, on the arms 4 and legs 6 of the patient 2. This recording as well as analog signal conditioning, take place in a recorder/signal conditioner 8 connected to the electrodes. In the recorder/signal conditioner 8, the large d.c. components contained in the ECG signal can be removed, together with further signal editing, to make possible a measurement of the ECG itself around the zero line. In this way, the dynamic range and the resolution required by the subsequent analog-to digital converter are reduced.

The output of the analog-to digital converter 10 is connected to an averager 12, which forms an average signal over a number of QRS complexes. This average signal is then subjected to forward filtering using a recursive IIR filter 14, preferably a Butterworth filter.

The output of the recursive IIR filter 14 is phase-shifted in an allpass filter 16, in which the latter part of the averaged complex is filtered in a time-reversed direction. The ringing introduced into the filtered signal by the IIR filter 14 is eliminated from the output signal from the allpass filter 16, permitting a more accurate measurement and analysis of this output signal.

The transfer function of a Butterworth filter employed as the recursive IIR filter 14 can be written as follows:

$$H_B(Z) = \frac{b_1 + b_2 Z^{-1} + b_3 Z^{-2} + b_4 Z^{-3} + b_5 Z^{-4}}{1 + a_2 Z^{-1} + a_3 Z^{-2} + a_4 Z^{-3} + a_5 Z^{-4}} = \frac{N(Z)}{D(Z)}$$

The allpass filter 16 is constructed by replacing the zero points of the Butterworth filter employed as the recursive IIR filter 14 with new zero points consisting of the poles of the filter reflected in the unity circle. The transfer function of the allpass-filter 16 then becomes:

$$H_A(Z) = \frac{Z^{-4} D(Z)^{-1}}{D(Z)} = \frac{a_5 + a_4 Z^{-1} + a_3 Z^{-2} + a_2 Z^{-3} + Z^{-4}}{1 + a_2 Z^{-1} + a_3 Z^{-2} + a_4 Z^{-3} + a_5 Z^{-4}}$$

The allpass filter 16 thus becomes a Butterworth filter with the same poles as the filter it is to compensate for, and the zero points are obtained by reflecting the poles in the unity circle in the Z-plane.

The phase shift of the allpass filter 16 then becomes $$\Phi_A(\omega) = -4\omega + \Phi_D(\omega) - \Phi_D(-\omega) = 2\Phi_D(\omega) - (4\omega)$$

wherein $\Phi_D(\omega)$=Phase shift for a filter with only zero points, i.e., $$H(Z) = \frac{1}{D(Z)} \text{ and}$$

$\Phi_D(-\omega) = -\Phi_D(\omega)$

The phase shift for the Butterworth filter is $$\Phi_B(\omega) = -2\omega + \Phi_D(\omega)$$

The total phase shift for the Butterworth filter forming the recursive IIR filter 14 cascaded with the allpass-filter 16 in the device according to the invention accordingly becomes the following, because the allpass filtering takes place in the backward direction:

$$\Phi_{total}(\omega) = \Phi_B(\omega) - \Phi_A(\omega) = -_D(\omega) + 2\omega = -\Phi_B(\omega)$$

The phase shift after the device according to the invention is thus the same as the phase shift obtained by backward filtering of the signal employing the Butterworth filter used as the recursive IIR filter 14. Any waveforms due to ringing are thus "moved" away from the area of interest, even though the original filtering was performed in forward direction in the conventional manner.

The method according to the invention for producing the allpass filter 16 begins using the Butterworth filter which produces the ringing to be eliminated, and replaces the zero points of this Butterworth filter with new zero points obtained by reflecting the poles of the Butterworth filter in the unity circle in the Z-plane. It is assumed that all of the zero points of the IIR filter are situated on the unity circle in the Z-plane. The phase shift for the allpass filter 16 thus becomes $$\Phi_A(\omega)=2*\Phi_H(\omega)+(n_H-n_A)\cdot\omega$$

wherein $\Phi_H(\omega)$=the phase shift of the Butterworth filter $n_H$=the number of zero points in the Butterworth filter $n_A$=the number of zero points in the allpass filter Because the Butterworth filter has as many zero points as poles, the second term becomes equal to zero. Otherwise, compensation must be made for a constant delay after the allpass filtering. It should be noted that the result of the filtering in the Butterworth filter employed as the recursive allpass filter 14, and the time-reversed allpass filtering which takes place in allpass filter 16, will not constitute filtering with a linear phase, but instead will constitute filtering with a phase response which is negated in relation to the phase response of the Butterworth filter, with optimum elimination of ringing being achieved for the applications in question.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for eliminating filter-produced ringing in filtered ECG signals comprising:

an analog-to-digital converter to which analog ECG signals are supplied, said converter converting said analog ECG signals into a series of digital values;

a recursive IIR filter to which said digital values are supplied, said recursive IIR filter filtering said digital values and generating an output signal exhibiting a phase shift and simultaneously introducing ringing into said output signal; and an allpass filter supplied with said output signal of said recursive IIR filter, said allpass filter filtering at least a portion of said output signal from said IR filter time-reversed in comparison to said IIR filter and with a phase shift equal to twice the phase shift exhibited by the output signal from the IIR filter to eliminate said ringing.

2. A device for eliminating filter-produced ringing in filtered EGG signals comprising:

an analog-to-digital converter to which analog EGG signals are supplied, said ECG signals each containing a QRS complex;

an averager supplied with said digital values, said averager forming a signal average over a number of said QRS complexes;

a recursive IIR filter to which said signal average is supplied, said recursive IIR filter filtering said signal average and generating an output signal exhibiting a phase shift and simultaneously introducing ringing into said output signal; and an allpass filter supplied with said output signal of said recursive IIR filter, said allpass filter filtering at least a portion of said output signal from said IIR filter time-reversed in comparison to said IIR filter and with a phase shift equal to twice the phase shift exhibited by the output signal from the IIR filter to eliminate said ringing.

3. A device as claimed in claim 1 wherein each of said ECG signals contains a QRS complex, and wherein said allpass filter comprises means for only filtering a latter part of each QRS complex.

4. A device as claimed in claim 1 wherein said ECG signals each contain a QRS complex, and wherein said allpass filter comprises means for only filtering an earlier part of each QRS complex.

5. A method for producing an allpass filter having a phase shift which is equal to twice the phase shift of an IIR filter having poles and having zero points situated on a unity circle in the Z-plane, comprising the steps of:

reflecting the poles of the IIR filter in the unity circle in the Z-plane to obtain new zero points; and replacing the zero points of said IIR filter with said new zero points.

* * * * *